(12) United States Patent
Hoberg

(10) Patent No.: US 8,618,464 B2
(45) Date of Patent: Dec. 31, 2013

(54) DEVICE AND METHOD FOR DETECTING BROKEN GLASS IN A CONVEYOR STERILIZATION TUNNEL

(75) Inventor: Karl Hoberg, Marburg (DE)

(73) Assignees: CSL Behring GmbH, Marburg (DE); Accuro GmbH, Marburg (DE)

( * ) Notice: Subject to any disclaimer, the term of this patent is extended or adjusted under 35 U.S.C. 154(b) by 349 days.

(21) Appl. No.: 13/057,440

(22) PCT Filed: Aug. 3, 2009

(86) PCT No.: PCT/EP2009/005601
§ 371 (c)(1),
(2), (4) Date: Feb. 3, 2011

(87) PCT Pub. No.: WO2010/015369
PCT Pub. Date: Feb. 11, 2010

(65) Prior Publication Data
US 2011/0133062 A1 Jun. 9, 2011

(30) Foreign Application Priority Data
Aug. 4, 2008 (DE) .......................... 10 2008 036 069

(51) Int. Cl.
*H01J 40/14* (2006.01)
(52) U.S. Cl.
USPC .......................................... 250/221; 345/556
(58) Field of Classification Search
USPC .......................................... 250/221; 345/556
See application file for complete search history.

(56) References Cited

U.S. PATENT DOCUMENTS

| | | | |
|---|---|---|---|
| 3,025,447 A * | 3/1962 | Early et al. ................... | 318/480 |
| 3,527,017 A | 9/1970 | Taylor et al. | |
| 6,979,814 B2 * | 12/2005 | Kudo et al. ................... | 250/221 |

FOREIGN PATENT DOCUMENTS

| | | |
|---|---|---|
| AT | 411 875 B | 7/2004 |
| DE | 41 15 235 C1 | 12/1992 |
| DE | 42 17 054 A1 | 11/1993 |
| DE | 42 10 157 C2 | 12/1994 |
| DE | 691 07 991 T2 | 4/1995 |
| EP | 0 570 946 B1 | 12/1996 |
| GB | 1 349 677 | 4/1974 |
| WO | WO 2006/029083 A2 | 3/2006 |

OTHER PUBLICATIONS

International Search Report from the European Patent Office for International Application No. PCT/EP2009/05601, mailing date Nov. 24, 2009.

* cited by examiner

*Primary Examiner* — Tony Ko
(74) *Attorney, Agent, or Firm* — Finnegan, Henderson, Farabow, Garrett & Dunner, LLP

(57) ABSTRACT

The invention relates to a device and a method for detecting broken glass in a continuous furnace provided for sterilizing or depyrogenating glass containers, comprising a transport device for the glass containers, wherein the detection device comprises at least one transmission and receiving unit. The receiving unit is designed to detect electromagnetic radiation that can be emitted by the transmission unit. The transport device and the transmission unit and receiving unit are positioned and aligned in relation to each other such that the glass particles or pieces of broken glass resulting from glass breakage cross the radiation path between transmission and receiving unit during or after leaving a substantially horizontal transport plane predetermined by the transport device.

14 Claims, 3 Drawing Sheets

Figure 1:
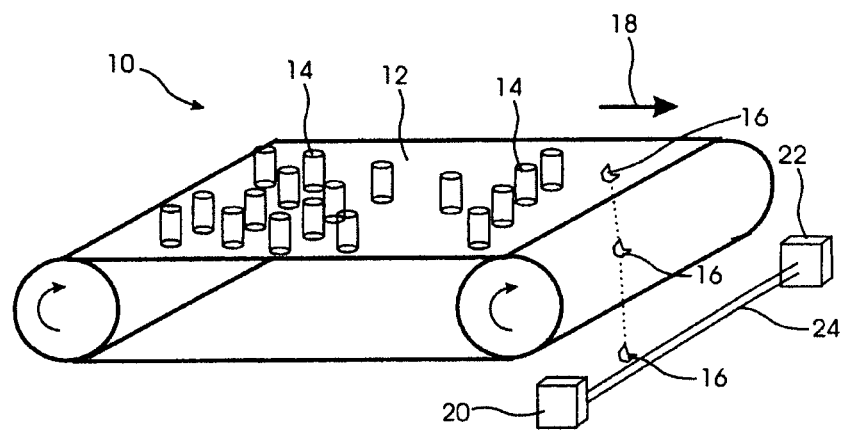

DEVICE AND METHOD FOR DETECTING BROKEN GLASS IN A CONVEYOR STERILIZATION TUNNEL

This application is a National Stage application under 35 U.S.C. §371 of International Application No. PCT/EP2009/005601, filed Aug. 3, 2009, which claims the benefit of priority of German Patent Application No. 10 2008 036 069, filed Aug. 4, 2008, both of which are incorporated herein by reference in their entirety.

The present invention relates to a device and a method for detecting broken glass in a continuous furnace which is intended to sterilize or depyrogenate glass containers and has, inter alia, a transport device for the glass containers.

PRIOR ART

Sterilization or depyrogenation devices in the form of a so-called sterilization tunnel are known as such from the prior art. They are predominantly used to sterilize or depyrogenate containers to be used in the pharmaceutical sector, in particular ampoules, carpules or containers made of tube glass, so-called vials.

Such sterilization tunnels are predominantly designed according to the continuous flow principle, the glass containers to be sterilized or depyrogenated being transported through different temperature zones inside the continuous furnace by means of a transport device which is typically in the form of a conveyor belt.

Such a continuous furnace is shown, for example, in DE 42 17 054 A1 and comprises an electrical heating register via which a fan allows the air heated to a sterilization temperature of 320° C., for example, to circulate in a recirculated air circuit. In this case, this recirculated air circuit leads from the fan, via HEPA filters which are resistant to hot air, from the top to the bottom through the sterilization channel in which the heating registers are also arranged.

In order to be able to achieve sufficient sterilization or depyrogenation, the glass containers to be sterilized or depyrogenated must be exposed to the predefined sterilization or depyrogenation temperature for a certain period of time which is typically in the minutes range. After this, the containers are cooled to a lower temperature level at which it is possible to fill and close the containers. The containers are heated and cooled with a relatively large temporal temperature gradient. Heating to the sterilization or depyrogenation temperature can thus be carried out within one minute or even in a considerably shorter interval of time.

On account of these system-dependent temperature fluctuations when passing through such a sterilization or depyrogenation tunnel but also on account of a dense, possibly even crowded arrangement of the glass containers on the transport device leading through the sterilization or depyrogenation tunnel, broken glass which is associated with the formation of very small glass particles or shards of glass may occasionally occur.

This is not only disadvantageous with respect to the respectively destroyed or damaged glass container, but rather, in particular when a glass container bursts due to thermal stresses in the material, the problem of the glass containers on the transport device, which are open to the top and are in the immediate vicinity of the burst glass container, being contaminated with glass particles arises.

The removal of such glass particles or shards of glass from the affected glass containers is extremely complicated. Admittedly, there are solution approaches for inverting the containers, turning them upside down as it were, and blowing them out with air in order to remove any shards or glass particles adhering in the containers. However, since the glass containers designed to accommodate pharmaceutical substances are provided as disposable and single-use articles anyway, such a method for removing shards of glass or glass particles is economically unprofitable.

At any rate, however, the situation in which a glass container which has been contaminated with glass particles produced by broken glass is filled with a pharmaceutical substance, for instance a liquid drug or a vaccine, should be avoided since the value of the pharmaceutical substance which can be accommodated in a single glass container may exceed up to 100 or 1000 times the production costs of a glass container.

OBJECT

The present invention is therefore based on the object of providing a system for detecting broken glass in a sterilization or depyrogenation tunnel, which system is as economical as possible, is simple to implement, is particularly simple to operate and, in addition, is reliable.

INVENTION AND ADVANTAGEOUS EFFECTS

The object on which the invention is based is achieved by means of a detection device according to patent claim 1 and a method for detecting broken glass according to patent claim 14. Advantageous embodiments of the invention are specified in the respective dependent patent claims.

The device according to the invention is designed to detect broken glass in a continuous furnace which is intended to sterilize or depyrogenate glass containers, the continuous furnace having at least one transport device for the glass containers, which transport device can be used to guide the glass containers through the continuous furnace. The continuous furnace has at least one such temperature range in which so-called pyrogens, that is to say flammable degradation products and residual cell constituents from germs which have been killed, are completely removed.

The detection device according to the invention is distinguished by at least one transmitting unit and one receiving unit, the receiving unit being designed at least to detect those electromagnetic beams which are emitted by the transmitting unit. In this case, provision is also made for the transport device of the continuous furnace and the transmitting and receiving units to be positioned and/or oriented with respect to one another in such a manner that glass particles or shards of glass from damaged or burst glass containers, which are produced by broken glass, cross the beam path between the transmitting unit and the receiving unit immediately when leaving or after leaving an essentially horizontal transport plane predefined by the transport device.

The glass particles produced by broken glass are preferably moved out of the transport plane under the force of gravity. As soon as a glass particle crosses the beam path between the transmitting unit and the receiving unit, the beam path is interrupted at least for a short period of time but is at least attenuated or changed in a manner which can be detected by the receiving unit. The glass particles which cross the beam path between the transmitting unit and the receiving unit are designed to change the beam path by refraction and/or reflection and/or to change the radiation intensity which can be detected at the receiving unit in the form of a detector.

The device according to the invention and the detection method to be implemented using said device are based on the knowledge that shards of glass produced when a glass container bursts or breaks, for instance an ampoule, a carpule, septum glass, syringes or vials, or other shards of glass produced when so-called parenteral packaging breaks come to lie in interspaces between the glass containers on the transport device. Since the transport device is typically in the form of a circulating conveyor belt, the glass particles produced on the belt by broken glass fall off the belt at a deflection point of the conveyor belt, typically at the end of a transport path, and are thus conveyed out of the transport plane predefined by the conveyor belt.

Appropriately arranging the transport device and the transmitting and receiving units with respect to one another makes it possible to contactlessly detect when glass particles fall off the transport device. As a result of such detection which can be made discernible to the operating personnel of the continuous furnace or the transport device using an acoustic or optical signaling device, the invention provides for a predefined number of containers arranged in the immediate vicinity of the burst and detected container to be prophylactically removed from the production, cleaning or filling cycle.

In this case, in particular, provision is made to also prophylactically remove, from a process station connected downstream of the continuous furnace, those containers which have already left the transport device when broken glass is detected so that it is possible to adequately ensure that all glass containers which have been potentially contaminated with glass particles and, on account of a single glass container being broken, are placed around the latter at the time at which said container is broken are removed from the production sequence.

Admittedly, a multiplicity of glass containers are prophylactically destroyed and/or fed to a recycling circuit where possible in this manner when a single glass breakage occurs. On account of the fact that broken glass can be detected in a particularly reliable and sufficiently safe manner using this method and it is necessary to manually intervene in the current production process only when an actual glass breakage occurs, the detection method which can be carried out using the present detection device is particularly efficient in terms of production.

In particular in view of the production costs for a single glass container and the frequency with which broken glass occurs, which can be stated as considerably less than 1 per thousand, prophylactic removal of a number of glass containers around a burst glass container is of no particular consequence.

One advantageous embodiment of the invention provides for the beams propagating between the transmitting unit and the receiving unit, in particular light beams in the visible or else infrared or ultraviolet spectral range, to run essentially perpendicular to the direction of movement of the glass particles or shards of glass. The direction of movement of the glass particles or shards of glass is used to mean, in particular, that direction of movement of the glass particles which is assumed by the latter after leaving the transport device.

The arrangement of the transmitting unit and the receiving unit beneath the transport device, in particular in the region of an end section of the transport device, which end section is at the front in the conveying direction, is particularly advantageous. This makes it possible to detect those glass particles or shards of glass which are produced by broken glass and come to lie on the transport device immediately when they fall off the detection device, for instance in the region of the deflection point of a transport device in the form of a conveyor belt.

In this case, provision is also made for the distance between the transmitting unit and the receiving unit to correspond at least to the width of the conveyor belt, with the result that all glass particles on the conveyor belt can be detected by the receiving unit when they cross the beam path irrespective of their transverse arrangement with respect to the transport direction.

Another particularly advantageous embodiment of the invention provides for a collecting device for glass particles or shards of glass to be arranged beneath and in relation to a front edge in the transport direction of the transport device. This collecting device may be in the form of a funnel, in particular, and may have such an extent or a corresponding funnel cross section, both in the conveying direction and obliquely or transversely to the latter, which adequately ensures that all glass particles or shards of glass conveyed using the transport device land in the collecting device.

In this case, one preferred development provides for the collecting device to have at least an extent which corresponds to the width of the transport device or to taper in a funnel-like manner at least in sections and/or to open, with an outlet, into a feed device for the transmitting and receiving units.

This feed device is preferably in the form of an inclined plane and is intended to allow the glass particles or shards of glass which have been received by the collecting device and are forwarded to the feed device to slide down. On account of its inclination which differs both from the perpendicular inclination and from the horizontal inclination, the feed device constitutes a defined plane in which the glass particles or shards of glass which slide along the feed device or slide down on the latter can be safely and reliably determined using the transmitting and receiving units.

In this case, provision is also made for at least the angle of inclination of the feed device or its inclined plane to be adjustable. This makes it possible to deliberately influence and control the speed of the glass particles sliding down along the feed device. In this case, the transmitting and receiving units are arranged at the foot or at a lower section of the feed device, the beam of electromagnetic radiation propagating between the transmitting and receiving units running essentially in the inclined plane of the feed device and perpendicular to the inclination direction of the latter.

In addition, provision can also be made for the orientation or the horizontal component of the feed device and of its inclined plane to be variable with respect to the conveying direction predefined by the transport device. This makes it possible to universally take into account, for instance, the installation space or space requirements in the region of the continuous furnace and/or downstream processing stations. In this case, it is conceivable, for example, to design the inclined plane as a guide plate which is arranged on a pivotable stand beneath an outlet of a collecting device in the form of a funnel.

The feed device advantageously tapers toward the transmitting and receiving units, with the result that the distance between the transmitting and receiving units can be selected to be correspondingly short, in particular less than the width of the transport device. The relatively dense arrangement of the transmitting and receiving units relative to one another makes it possible to minimize such disturbances which influence detection. As a result of this, the entire detection device also becomes more insensitive to mechanical vibrations.

Furthermore, the invention provides for the transmitting and receiving units to be arranged on opposite side edges of the transport device or the feed device. This allows the beams running between the transmitting and receiving units to propagate in the plane of the transport device and/or in the plane of the feed device or to each run essentially parallel thereto.

In particular, provision can be made in this case for the transmitting and receiving units to be arranged or oriented with respect to the conveyor belt in such a manner that the beams propagating between the transmitting and receiving units run both essentially perpendicular to the transport direction of the conveyor belt and essentially perpendicular to the surface normal of the conveyor belt. The beams therefore preferably scan the entire width of the conveyor belt or the feed device connected downstream of the conveyor belt, with the result that all broken glass produced can be safely and reliably detected.

Provision is also made for the transmitting unit to be in the form of a monochromatic light source, for instance in the form of a laser light source. This can be operated either in a pulsed mode or in a so-called continuous wave mode, that is to say with a beam which continuously emits light. In the pulsed mode, it should be ensured, in particular, that the pulse frequency is so high that the interval of time between two successive pulses is shorter than that interval of time needed by a glass particle to cross the beam path between the transmitting and receiving units.

Irrespective of the method of operation of the transmitting unit, it should also be ensured that the scanning rate of the detection unit, which may be in the form of a photodiode in the simplest case, is suitable for the speed and size of the glass particles, with the result that no glass particles slide past the detection device without detection.

One development or alternative refinement of the invention can also provide for the transport device to be in the form of a conveyor belt which is provided with a grating mesh and has a multiplicity of openings, and for a plurality of transmitting and receiving units to be arranged in pairs and at a distance from one another in the conveying direction along the movement path to be covered by the transport device. In this case, provision may be made, in particular, for a type of light or radiation plane to be formed beneath the conveyor belt running in the conveying direction by means of an appropriate optical system or a plurality of transmitting and receiving units, which light or radiation plane is intended to detect the glass particles passing through the interspaces of the conveyor belt immediately when broken glass occurs.

This makes it possible to detect broken glass virtually without a time delay. The location of the broken glass, for example, can also be precisely determined by means of such a conveying device and the multiplicity of individual transmitting and receiving devices, with the result that manual intervention in order to remove a number of containers possibly contaminated with glass particles can be carried out even before glass particles fall off the end of the transport device.

The invention also provides for the receiving unit to be coupled to at least one evaluation unit which is designed to generate an acoustically and/or optically perceptible warning signal. A flashing light or warning light, for example, is suitable for generating an optically perceptible warning signal, whereas a horn, a siren or an instrument which produces a comparable alarm can be used as the acoustic signal generator.

In this case, provision is also made for the evaluation unit to be coupled to a control unit of the continuous furnace and/or of the conveying device, with the result that the continuous furnace and/or its conveying device can be automatically switched off or stopped immediately when a glass breakage event is detected or immediately after a glass breakage event has been detected.

According to another independent aspect, the invention relates to a method for detecting broken glass in or on a continuous furnace which is intended to sterilize or depyrogenate glass containers, the continuous furnace having at least one transport device for the glass containers, which transport device is used to guide the glass containers through the continuous furnace. In this case, provision is also made for at least some but preferably all of the glass particles or shards of glass leaving a transport plane predefined by the transport device to be detected using electromagnetic radiation which propagates between a transmitting unit and a receiving unit.

In this case, detection is carried out while leaving or after leaving a circulating conveyor belt of the conveying device. The detected event is then acoustically and/or optically signaled to the operating personnel of the continuous furnace and/or used to automatically stop or interrupt at least the transport device.

EXEMPLARY EMBODIMENTS

Figure 2:
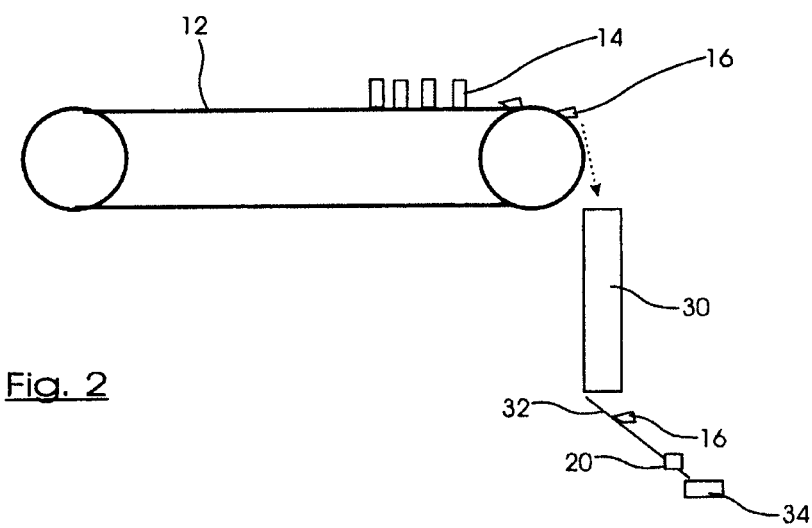
Figure 3:
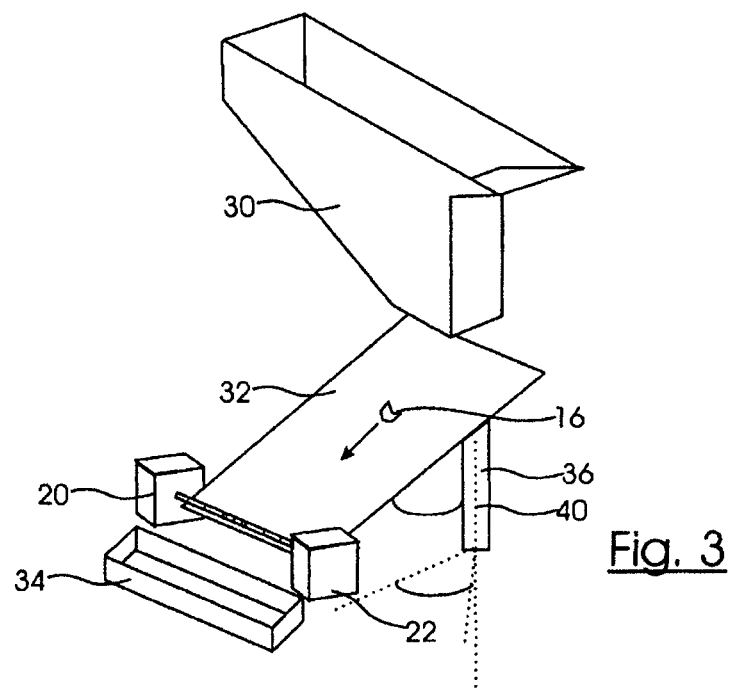
Figure 4:
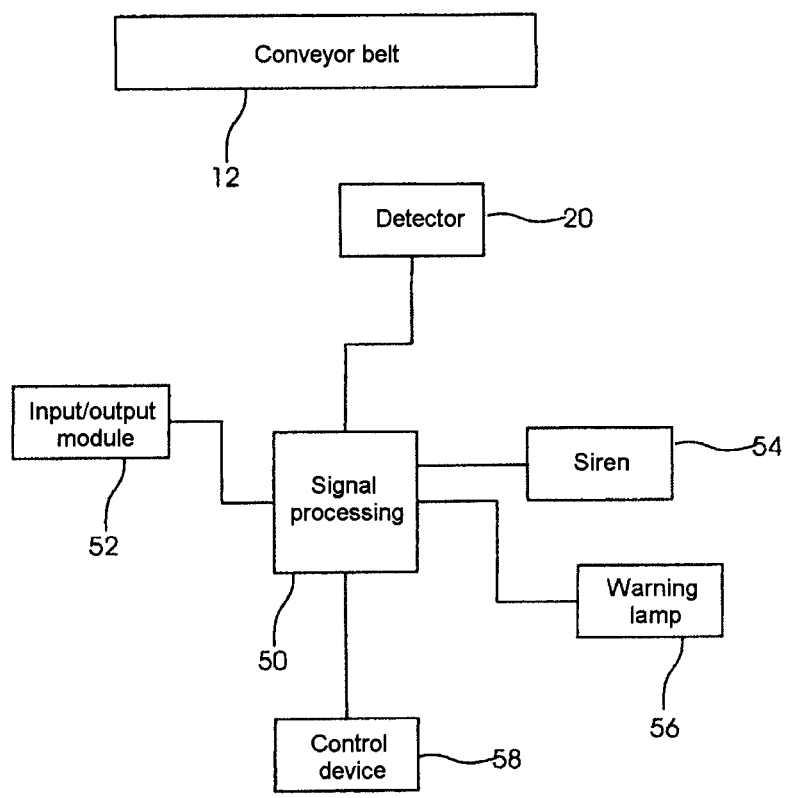

Further aims, features and advantageous possible uses of the invention emerge from the following description of exemplary embodiments. In this case, all of the features literally described above and below and diagrammatically illustrated in the figures in any useful combination form the subject matter of the present invention. In the drawing:

FIG. 1 shows a diagrammatic perspective illustration of the conveying device and an associated transmitting unit and receiving unit, FIG. 2 shows a diagrammatic side view of another embodiment with a collecting device and a feed device, FIG. 3 shows a perspective diagrammatic illustration of the collecting device and feed device, and FIG. 4 shows a block diagram of an electrical evaluation unit and thus coupled components.

The transport device 10 shown in FIG. 1 has a circulating conveyor belt 12 which may be in the form of a grating mesh, for example, in order to allow hot air to flow through vertically inside the continuous furnace not explicitly shown in the figures. The conveyor belt 12 is loaded with a multiplicity of glass containers 14, which may be open to the top, from the left, which containers are conveyed through the sterilization or depyrogenation tunnel (not explicitly shown in the figures) by means of the conveyor belt 12, the glass containers 14 being heated to the sterilization or depyrogenation temperature, for instance in the region of 300° C., within a very short time and also being heated for a predefined amount of time.

Even though interspaces between individual containers 14 can be seen in FIG. 1, the containers are typically fed to the transport device tightly pressed to one another and touching one another. The practice of tightly placing individual, often cylindrical or elongate glass containers 14 next to one another or together prevents the containers from falling over, in particular when the conveyor belt 12 is moved in the conveying direction indicated by the arrow 18.

In addition to the glass containers 14, individual shards of glass or glass particles 16 which do not fall through the grating mesh of the conveyor belt 12 may remain on the conveyor belt 12 in interspaces between surrounding glass containers 14 as a result of an individual glass container 14 or a plurality of glass containers 14 bursting or shattering. These glass particles 16 are moved by the conveyor belt to the right in the conveying direction, where they fall down owing to gravity at the end of the movement path as a result of the conveyor belt being deflected on a deflection roller.

This falling movement of glass particles or shards of glass 16 can be detected using a detection device having a receiving unit 20 and an associated transmitting unit 22 for electromagnetic radiation 24. In one simple refinement, the detection device 20, 22 may be arranged at the end of the movement path of the conveyor belt 12 somewhat beneath the deflection roller which is on the right in the transport direction. In principle, it is sufficient to form the detection device as a light barrier, even though the implementation of a laser light source as a transmitting unit, in particular based on a semiconductor, can be considered to be advantageous.

In the refinement according to FIG. 1, the receiving unit 20 and the transmitting unit 22 are preferably arranged to the side of the conveyor belt 12, with the result that the electromagnetic radiation propagating essentially parallel to the plane of the conveyor belt 12 can reliably detect all broken glass falling off the conveyor belt 12. In this case, the transmitting unit 22 and the receiving unit 20 are arranged to the left and right of a lower end section of the feed device 32.

As soon as a glass particle 16 which falls off the transport device 10 crosses the beam path 24, it can be detected using the detector unit 20 and, once converted into a signal which can be evaluated electrically, can be forwarded to an evaluation unit 50 illustrated by way of example in FIG. 4. As a result of the detection and brief interruption or attenuation of the signal which can be detected by the receiving unit 20, the evaluation unit can use an acoustic signal generator 54 and/or an optical signal generator 56 to make the glass breakage event discernible to the operating personnel of the continuous furnace.

In addition, provision can be made for the evaluation unit 50 to be coupled directly to a control unit 58 either of the entire continuous furnace or its transport device 10, with the result that the conveyor belt 12 can also be stopped without intervention from operating personnel in order to prophylactically remove glass containers 14 which have possibly been contaminated with glass particles. In addition, it is also conceivable to remove a predefined number, for instance a few rows of glass containers 14, from the production cycle manually or by machine without stopping the transport device 12.

Provision is also made for the evaluation unit 50 to be coupled to an input and output module 52 which can be used, for example, to set a triggering threshold for an alarm signal or else the type of alarm to be produced. The detection of continuous glass breakage events can also be documented and evaluated using the input and output device 52.

FIGS. 2 and 3 diagrammatically represent another embodiment of the invention. In this case, a collecting device 30 in the form of a funnel is arranged between a deflection roller of the conveyor belt 12 and the transmitting and receiving units 20, 22. Connected downstream of said collecting device is a feed device 32 which is in the form of an inclined plane and guides the glass particles collected by the collecting device 30 in a controlled manner through the light barrier 24 formed between the transmitting and receiving units 22, 20.

In this case, the inclined plane 32 of the feed device may be arranged on a holder 36 in such a manner that its angle of inclination can be adjusted so that the speed or a speed bandwidth of the glass particles 16 crossing the light barrier 24 can be deliberately set by selecting a suitable angle of inclination α. Arranged beneath and at the end of the inclined plane 32 is a collecting container 34 in which the glass particles or shards of glass 16 which are collected and can be detected using the light barrier 24 can ultimately be collected.

In addition to the option of adjusting the angle of inclination α, provision may also be made to also orient the horizontal component of the inclined plane 32 in a variable manner. In particular, provision may be made to rotate the entire feed device 32 about an angle θ with respect to a pivot axis 40 which preferably runs through the holder 36. In this manner, the horizontal component of the inclined plane 32 can extend, for instance, in the conveying direction, counter to the conveying direction or obliquely with respect to the latter, in particular in a perpendicular manner. This makes it possible to universally couple the entire detection device to already existing transport devices and/or continuous furnaces and to individually adapt it to the external or internal dimensions of the latter.

LIST OF REFERENCE SYMBOLS

10 Transport device
12 Conveyor belt
14 Glass container
16 Shard of glass
18 Arrow
20 Detector
22 Transmitter
24 Beam path
30 Collecting device
32 Feed device
34 Collecting container
36 Holder
40 Pivot axis
50 Evaluation unit
52 Input/output module
54 Acoustic signal generator
56 Optical signal generator
58 Control unit

The invention claimed is:

1. A device for detecting broken glass in a continuous furnace which is intended to sterilize or depyrogenate glass containers, comprising: a transport device configured to transport the glass containers, the transport device defining a substantially horizontal transport plane;
a transmitting unit;
a receiving unit, the receiving unit configured to detect electromagnetic radiation emitted by the transmitting unit;
wherein the transport device and the transmitting and receiving units are positioned and oriented with respect to one another such that glass particles or shards of glass cross a beam path between the transmitting unit and the receiving unit when leaving or after leaving the essentially horizontal transport plane.

2. The device as claimed in claim 1, wherein the beam path is configured to extend between the transmitting unit and the receiving unit and run substantially perpendicular to a conveying direction of the glass particles or shards of glass.

3. The device as claimed in claim 1, wherein the transmitting unit and the receiving unit are arranged beneath the transport device.

4. The device as claimed in claim 3, wherein the transmitting unit and the receiving unit are arranged proximate to an end section of the transport device, wherein the end section is at a front of the transport device in the conveying direction.

5. The device as claimed in claim 1, further comprising a collecting device configured to collect the glass particles or shards of glass, wherein the collecting device is arranged beneath and in alignment with a front edge of the transport device (12) in a transport direction of the transport device.

6. The device as claimed in claim 5, wherein the collecting device includes at least one of a dimension which corresponds to a width of the transport device, a funnel-like configuration, and an opening having an outlet into a feed device for the transmitting and receiving units.

7. The device as claimed in claim 5, further comprising a feed device, the feed device having an adjustable inclined plane configured to guide the glass particles or shards to the transmitting and receiving units arranged on a lower end section of the feed device.

8. The device as claimed in claim 7, wherein the feed device is configured to taper in a direction toward the transmitting and receiving units.

9. The device as claimed in claim 7, wherein the transmitting and receiving units are arranged on opposite side edges of the transport device or the feed device such that electromagnetic radiation running between the transmitting and receiving units runs along the beam path.

10. The device as claimed in claim 1, wherein at least one of the transmitting unit and the receiving unit are configured to be operated in a pulsed or a continuous wave mode.

11. The device as claimed in claim 1, wherein the transport device includes a conveyor belt having a grating mesh with a plurality of openings, wherein the transmitting unit includes a plurality of transmitting units and the receiving unit includes a plurality of receiving units, wherein the plurality of transmitting and receiving units are arranged in pairs and distanced from one another in a conveying direction along a displacement path.

12. The device as claimed in claim 1, further comprising an evaluation unit coupled to the receiving unit, the evaluation unit configured to generate at least one of an acoustically perceptible and optically perceptible warning signal.

13. The device as claimed in claim 12, further comprising a control unit coupled to the evaluation unit, the control unit configured to control at least one of the continuous furnace and the transport device for an emergency shutdown of at least one of the continuous furnace and the transport device.

14. A method for detecting broken glass in or on a continuous furnace configured to sterilize or depyrogenate glass containers, comprising:
    guiding glass containers through the continuous furnace with a transport device, the transport device defining a transport plane along which glass particles or shards of glass are transported; and
    detecting the glass particles or shards of glass as they exit the transport plane using electromagnetic radiation which propagates between a transmitting unit and a receiving unit.

* * * * *